US012697437B2

(12) United States Patent
Helmer et al.

(10) Patent No.: US 12,697,437 B2
(45) Date of Patent: Aug. 4, 2026

(54) ROTATION SENSOR FOR AN INJECTION DEVICE

(71) Applicant: SANOFI, Paris (FR)

(72) Inventors: Michael Helmer, Frankfurt am Main (DE); Christian Rehbein, Nieder-Olm (DE)

(73) Assignee: SANOFI, Paris (FR)

( * ) Notice: Subject to any disclaimer, the term of this patent is extended or adjusted under 35 U.S.C. 154(b) by 1373 days.

(21) Appl. No.: 16/954,372

(22) PCT Filed: Dec. 17, 2018

(86) PCT No.: PCT/EP2018/085112
§ 371 (c)(1),
(2) Date: Jun. 16, 2020

(87) PCT Pub. No.: WO2019/121448
PCT Pub. Date: Jun. 27, 2019

(65) Prior Publication Data
US 2021/0085874 A1 Mar. 25, 2021

(30) Foreign Application Priority Data

Dec. 18, 2017 (EP) .................................... 17306803

(51) Int. Cl.
*A61M 5/24* (2006.01)
*A61M 5/315* (2006.01)
*G01B 5/24* (2006.01)

(52) U.S. Cl.
CPC ............ *A61M 5/24* (2013.01); *A61M 5/3158* (2013.01); *G01B 5/24* (2013.01); *A61M 5/31551* (2013.01); *A61M 2205/332* (2013.01)

(58) Field of Classification Search
CPC .. A61M 5/24; A61M 5/3158; A61M 5/31551; A61M 2205/332; G01B 5/24
See application file for complete search history.

(56) References Cited

U.S. PATENT DOCUMENTS 8,556,847 B2 10/2013 Kohlbrenner et al.
8,777,899 B2 7/2014 Nicholls et al.
(Continued)

FOREIGN PATENT DOCUMENTS

CN 104147664 11/2014
CN 106415227 2/2017
(Continued)

OTHER PUBLICATIONS

PCT International Preliminary Report on Patentability in International Appln. No. PCT/EP2018/085112, dated Jun. 23, 2020, 6 pages.

(Continued)

*Primary Examiner* — Lauren P Farrar
(74) *Attorney, Agent, or Firm* — Bond, Schoeneck & King, PLLC

(57) ABSTRACT

The present disclosure relates to a rotation sensor for an injection device, the rotation sensor comprising:
  a rotatable element configured for a mechanical engagement with a ratchet mechanism, the rotatable element comprising an outer rim and a hub
is configured for transmission of a torque between the outer rim and the hub,
  at least one sensor attached to the rotatable element and configured to measure at least one of a mechanical force, a mechanical pressure or a mechanical strain at a portion of the rotatable element during a rotation of the rotatable element,
  a processor connected to the at least one sensor and configured
to calculate an angle of rotation of the rotatable element on the basis of a sensor output of the at least one sensor.

21 Claims, 4 Drawing Sheets

(56) References Cited

U.S. PATENT DOCUMENTS

| | | | |
|---|---|---|---|
| 10,383,996 B2 | 8/2019 | Miller et al. | |
| 2002/0029018 A1 | 3/2002 | Jeffrey | |
| 2007/0021715 A1 | 1/2007 | Kohlbrenner et al. | |
| 2010/0238038 A1 | 9/2010 | Kohlbrenner et al. | |
| 2016/0015903 A1* | 1/2016 | Madsen | A61M 5/31568 604/211 |
| 2017/0153156 A1 | 6/2017 | Nitz et al. | |
| 2017/0205296 A1* | 7/2017 | Bradford | G01L 5/1627 |
| 2017/0326303 A1 | 11/2017 | Eardley et al. | |
| 2018/0050160 A1 | 2/2018 | Bilton et al. | |
| 2018/0161503 A1* | 6/2018 | Windum | A61M 5/24 |
| 2019/0009032 A1* | 1/2019 | Hautaviita | A61M 5/3157 |
| 2019/0209783 A1 | 7/2019 | Utermoehlen et al. | |

FOREIGN PATENT DOCUMENTS

| | | |
|---|---|---|
| CN | 106714878 A | 5/2017 |
| CN | 106794319 | 5/2017 |
| CN | 107405449 A | 11/2017 |
| DE | 102016208622 | 11/2017 |
| JP | 2008-516711 | 5/2008 |
| JP | 2008216014 A | 9/2008 |
| JP | 2010-046508 | 3/2010 |
| WO | WO 2004/078239 | 9/2004 |
| WO | WO 2004/078240 | 9/2004 |
| WO | WO 2004/078241 | 9/2004 |
| WO | 2009132778 A1 | 11/2009 |
| WO | WO 2012/046199 | 4/2012 |
| WO | WO 2015/071354 | 5/2015 |
| WO | 2016091840 A1 | 6/2016 |
| WO | 2017009102 A1 | 1/2017 |
| WO | 2017041972 A1 | 3/2017 |
| WO | WO 2017/114911 | 7/2017 |

OTHER PUBLICATIONS

PCT International Search Report and Written Opinion in International Appln. No. PCT/EP2018/085112, dated Feb. 26, 2019, 8 pages.

* cited by examiner

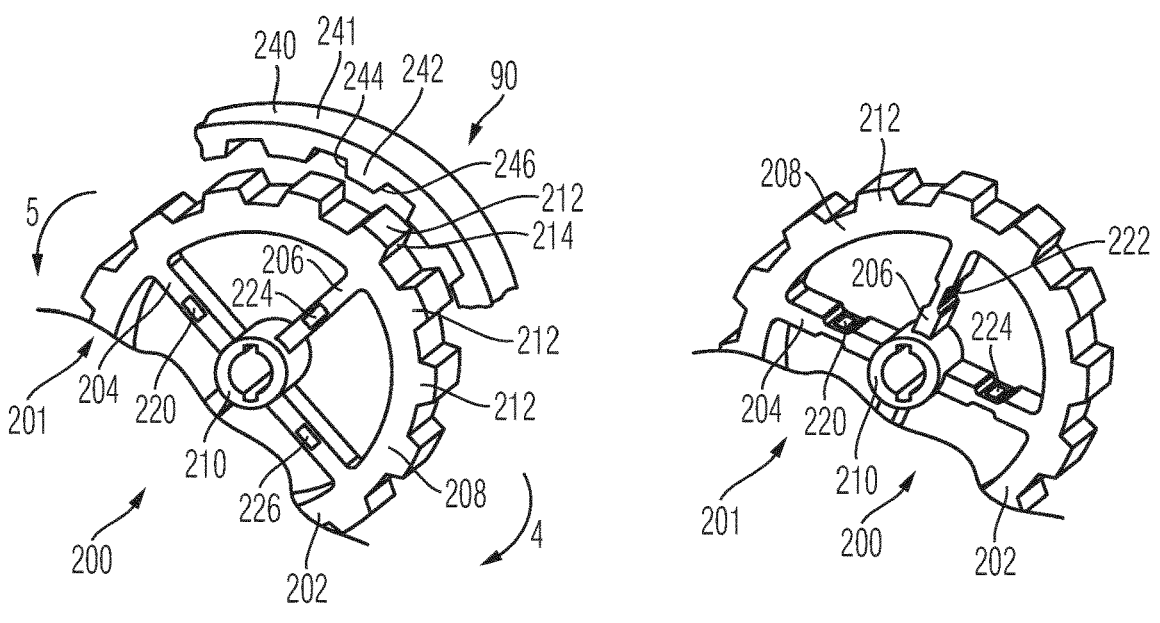
Fig. 5                          Fig. 6
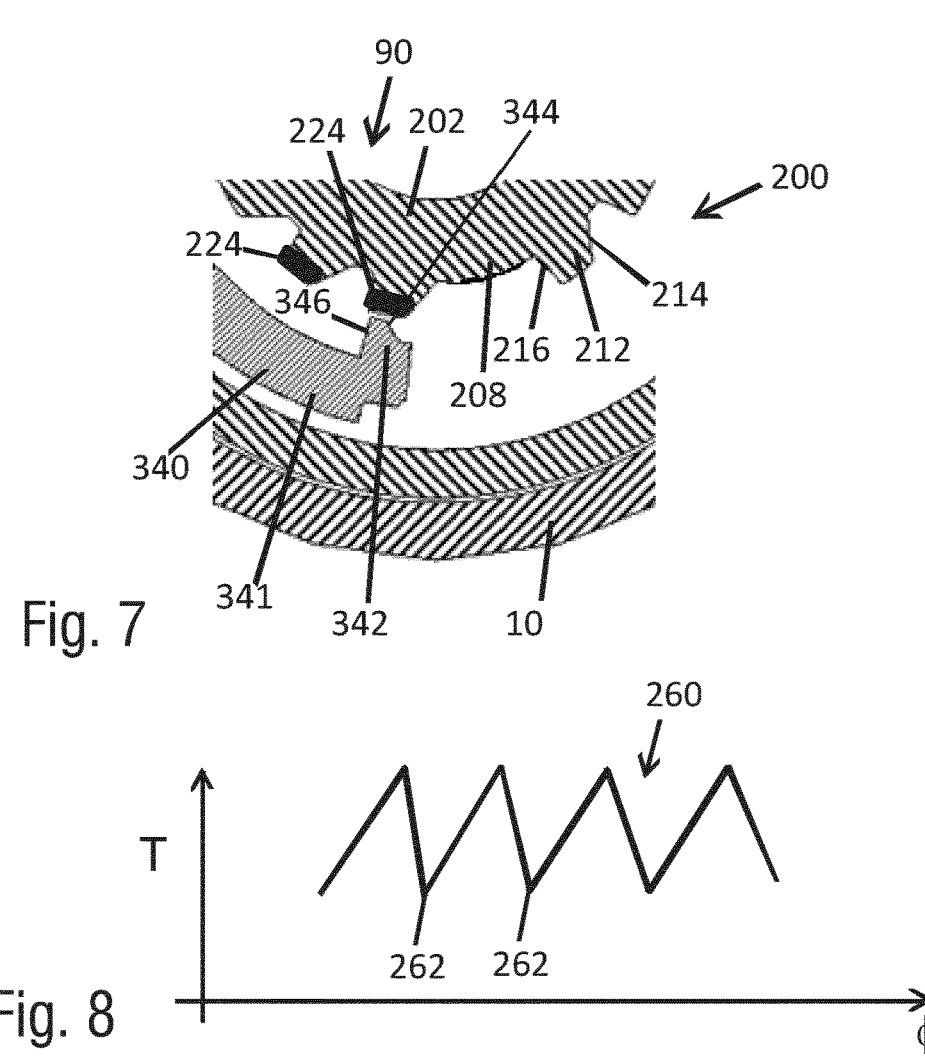
Fig. 7
Fig. 8

ROTATION SENSOR FOR AN INJECTION DEVICE

CROSS REFERENCE TO RELATED APPLICATIONS

The present application is the national stage entry of International Patent Application No. PCT/EP2018/085112, filed on Dec. 17, 2018, and claims priority to Application No. EP 17306803.2, filed on Dec. 18, 2017, the disclosures of which are incorporated herein by reference.

TECHNICAL FIELD

The present disclosure relates to the field of rotation sensors, in particular to rotation sensors configured for detecting and/or quantitatively measuring a rotation of a component of an injection device. In one aspect the disclosure relates to a rotation sensor implemented in an add-on device configured for attachment to an injection device. In one aspect the disclosure relates to a rotation sensor implemented in an injection device. In a further aspect the disclosure relates to an injection device equipped with a rotation sensor configured to detect and/or configured to quantitatively measure a rotation of the component of the injection device. In a further aspect the disclosure relates to a method of determining and/or quantitatively measuring a rotation of a component of an injection device.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, such as pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Such injection devices should provide setting and subsequent dispensing of a dose of a medicament of variable size. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod to operably engage with a bung or piston of the cartridge. By means of the drive mechanism and its piston rod, the bung or piston of the cartridge is displaceable in a distal or dispensing direction and may therefore expel a predefined amount of the medicament via a piercing assembly, e.g. in form of an injection needle, which is to be releasably coupled with a distal end section of the housing of the drug delivery device.

The medicament to be dispensed by the drug delivery device may be provided and contained in a multi-dose cartridge. Such cartridges typically comprise a vitreous barrel sealed in distal direction by means of a pierceable seal and being further sealed in proximal direction by the bung. With reusable drug delivery devices an empty cartridge is replaceable by a new one. In contrast to that, drug delivery devices of disposable type are to be entirely discarded when the medicament in the cartridge has been dispensed or used-up.

With some drug delivery devices, such as pen-type injection devices a user has to set a dose of equal or variable size by rotating a dose dial in a clockwise or dose-incrementing direction relative to a body or housing of the injection device. For injecting and expelling of a dose of a liquid medicament the user has to depress a trigger or dose button in a distal direction and hence towards the body or housing of the injection device. Typically, the user uses his thumb for exerting a distally directed pressure onto the dose button, which is located at a proximal end of the dose dial and the dose dial sleeve, while holding the housing of the injection device with the remaining fingers of the same hand.

For mechanically implemented injection devices it is desirable to enable a precise, reliable and quasi-automated supervision and/or collection of injection-related data during use of the injection device. Mechanically operated injection devices may be equipped with an electronically implemented add-on device or data collection device configured to monitor user-induced operation of the injection device. A data collection device for attachment to an injection device should be rather compact with regards to its geometric size. For data collection devices configured for attachment to mechanically implemented injection devices it is a challenge to detect and/or to quantitatively measure the manual operation of the device conducted by the user of the device, e.g. when a user rotates a dial member of the injection device during setting of a dose or when a rotatable component of the injection device is subject to rotation during expelling of a dose.

But also with electronically implemented injection devices, e.g. injection device equipped with an electric drive it is desirable to provide a precise, reliable and failure safe quantitative measuring of rotatable components of the injection device.

SUMMARY

In certain aspects, an improved rotation sensor configured to detect and/or to quantitatively measure a rotation of a rotatable component of an injection device is provided. The rotation sensor and the sensor principle can be universally applicable to injection devices as well as to add-on devices configured for attachment to such injection devices.

The rotation sensor can be generally applicable to a variety of different rotatable components of an injection device or of an add-on device. The rotation sensor can be cost efficient to manufacture and should feature a rather compact design and geometry.

In one aspect the disclosure relates to a rotation sensor for an injection device. The rotation sensor comprises a rotatable element configured for a mechanical engagement with a ratchet mechanism. The rotatable element comprises an outer rim and a hub. It is configured for transmission of a torque between the outer rim and the hub. The rotation sensor further comprises at least one sensor attached to the rotatable element and configured to measure at least one of a mechanical force, a mechanical pressure or a mechanical strain at a portion of the rotatable element during a rotation of the rotatable element. The rotation sensor further comprises a processor connected to the at least one sensor and configured to calculate an angle of rotation of the rotatable element on the basis of a sensor output of the at least one sensor.

The rotation sensor is universally applicable and/or implementable with injection devices or add-on devices configured for attachment to such injection devices. The rotation sensor may be implemented in an add-on device, such as a monitoring device configured to monitor operation of the injection device. Alternatively, the rotation sensor may be implemented in the injection device. The ratchet mechanism may be located in an add-on device or in the injection device, e.g. in a drive mechanism or in a dose setting mechanism of an injection device.

The ratchet mechanism typically comprises a first and a second component that are in a ratchet engagement. The first and the second components are rotatable relative to each other. One of the first and the second components comprises inclined teeth and the other one of the first and second component comprises at least one pawl or detent engaged with the inclined teeth so that a rotational motion of the first component relative to the second component can be imparted, governed or prevented. The mechanical engagement, i.e. a torque proof or rotational coupling between the rotatable element and the ratchet mechanism leads to a variation of a torque between the outer rim and the hub of the rotatable element, wherein the torque varies with the angle of rotation of rotatable element. By means of the at least one sensor the rotation dependent variations of a torque transmission across the rotatable element can be detected or can be quantitatively measured.

During the rotation of the rotatable element the ratchet mechanism is also subject to a rotation. The pawl or detent of the second component of the ratchet mechanism regularly engages with consecutive teeth of the first component of the ratchet mechanism. Every time a tooth of the first component passes a pawl or detent of the second component of the ratchet mechanism the torque across the rotatable element remarkably rises or drops. Such a rise or drop in the torque across the rotatable element can be detected by the at least one sensor and can be further processed by the processor. Every detected positive or negative peak of the torque across the rotatable element is an indication, that the components of the ratchet mechanism have been rotated by a discrete step as determined by the periodicity of the toothed structure of the first component and/or of the number and location of the pawls or detents of the second component of the ratchet mechanism.

The presently proposed rotation sensor is beneficial in that it can be attached to an injection device or can be implemented in an injection device in a variety of different ways. The rotation sensor may be implemented with an existing rotatable element of an injection device or of an add-on device. The rotation sensor may require a modification of only one component of an existing injection device or of an add-on device. The rotatable element may only have to be equipped with the at least one sensor and with the processor.

In some examples the rotatable element belongs to the ratchet mechanism. Here, the rotatable element may represent a first or a second component of the ratchet mechanism. The rotatable element may comprise a toothed structure to engage with at least a pawl or detent of a second component of the ratchet mechanism. In another example the rotatable element may comprise at least a pawl or detent and may form a second component of the ratchet mechanism that is in ratchet engagement with a toothed structure of a first component of the ratchet mechanism.

According to another example the at least one sensor is arranged on the outer rim. In this example the rotatable element is a part or forms a part of the ratchet mechanism. When arranged on the outer rim the sensor is configured to mechanically engage with another component of the ratchet mechanism. For instance, the rotatable element may constitute a first component of a ratchet mechanism featuring a toothed structure on an outside circumference to engage with at least a pawl or detent of a second component of the ratchet mechanism. By having the sensor located on the outer rim it may directly mechanically engage with the pawl or detent of the second component of the ratchet mechanism.

The at least one sensor may be located on the toothed structure of the first component of the ratchet mechanism. Every time the at least one sensor engages with the pawl or detent of the second component this will be detected by the at least one sensor. The at least one sensor may comprise a mechanical force sensor, a mechanical pressure sensor or a mechanical contact sensor. There may be provided a plurality of sensors along the circumference of the outer rim. It is conceivable, that every tooth of a toothed structure of the rotatable element comprises a separate sensor. For this, the processor may be individually connected to any one of the sensors. The rotation sensor is then not only configured to determine a rotation angle but is also configured to determine an angular position of the rotatable element, e.g. relative to a housing of the injection device or of the add-on device.

According to another example the rotatable element comprises at least two spokes. The outer rim and the hub are connected via the at least two spokes. When having only two spokes, the spokes are typically located diametrically opposite to each other with regards to the centrally located hub of the rotatable element. With three spokes the individual spokes may be separated in tangential or circumferential direction of the rotatable element by about 120°. With four spokes the angular separation between individual spokes may be about 90° and so on. Typically, the spokes are equidistantly separated with regard to the tangential or circumferential direction of the outer rim.

By means of at least two of more spokes the total weight of the rotatable element can be reduced compared to a configuration, wherein the rotatable element is configured as a solid disc having an outer rim and a hub. By means of the at least two spokes a transmission of a torque between the outer rim and the central hub can be easily detected and determined by means of the at least one sensor.

Typically, the at least two spokes, the outer rim and the hub are integrally formed. The rotatable element may comprise a rotatable wheel. The outer rim may comprise a circular structure and the spokes may each comprise a rather straight-shaped slab like structure extending radially inwardly from the outer rim towards the hub. The rotatable element or the rotatable wheel may comprise a rubber wheel, a plastic wheel or a metal wheel. The specific material the rotatable element is made of may depend on the type of sensor attached to the rotatable element.

According to another example the at least one sensor is attached to at least one of the at least two spokes. In further embodiments it is conceivable, that any of the at least two spokes is provided with a separate sensor. Here, the sensors attached to individual spokes may be substantially identical or they may belong to the same type of sensor. Furthermore it is conceivable, that there are arranged several sensors to one of the at least two spokes or that any of the at least two spokes is provided with a plurality of sensors.

By arranging the at least one sensor to at least one of the at least two spokes a transmission of a torque between the outer rim and the hub can be precisely detected by means of at least one of mechanical force sensor, a mechanical pressure sensor or a mechanical strain sensor. The spokes may be subject to an elastic deformation as a torque is transmitted between the outer rim and the hub. This elastic deformation can be detected or quantitatively determined by the at least one sensor when attached to at least one of the at least two spokes. Rather filigree or slim sized spokes may exhibit a well-defined elastic deformation behavior as a torque is applied to the rotatable element. By arranging the at least one sensor to at least one of the at least two spokes such an elastic deformation indicative of a variation of the torque transmitted between the outer rim and the hub can be precisely detected and/or quantitatively determined.

According to another example at least one of the at least two spokes comprises an outer portion connected to the outer rim, an inner portion connected to the hub and a middle portion connecting the outer portion and the inner portion. One of the inner portion, the middle portion and the outer portion comprises a cross-section that is smaller than a cross-section of another one of the inner portion, the middle portion and the outer portion. Hence, at least one of the at least two spokes comprises a heterogeneous cross-section or a varying cross-section along its radial extension. A variation of the cross-section of at least one spoke is beneficial for that the respective spoke exhibits a well-defined elastic deformation behavior as a torque is applied to the rotatable element. Typically, the spoke exhibiting a heterogeneous or variable cross-section along its radial extension is equipped and provided with at least one sensor.

According to another example the cross-section of the middle portion of the at least one spoke is smaller than the cross-section of at least one of the outer portion and the inner portion. In some examples the cross-section of the middle portion is smaller than the cross-section of the outer portion and is also smaller than the cross-section of the inner portion. Here, the outer portion and the inner portion of the spoke may comprise a substantially identical cross-section. In this way, the middle portion of the respective spoke comprises or constitutes a structurally weakened structure of the respective spoke. That portion of the respective spoke comprising a reduced cross-section compared to other portions of the spoke may be provided with the at least one sensor.

According to another example the at least one sensor is arranged to one of the inner portion, the middle portion and the outer portion having a cross-section that is smaller than a cross-section of another one of the inner portion, the middle portion and the outer portion. In this way, that section or portion of the at least one spoke featuring a reduced cross-section and exhibiting a well-defined mechanical or elastic deformation behavior is equipped and connected to the at least one sensor. Insofar, a mechanical or elastic deformation of a portion of the spoke can be precisely detected and/or quantitatively measured.

In further examples the at least one spoke comprises or exhibits a reduced cross-section in the inner portion, i.e. adjacent to the hub and/or in the outer portion, i.e. adjacent to the rim.

It is conceivable, that the middle portion comprises a cross-section that is larger than a cross-section of both, the inner portion and the outer portion. With such a configuration there may be arranged two sensors to the respective spoke. One sensor may be attached to the inner portion of the spoke and the other sensor may be attached to the outer portion of the respective spoke. When the rotatable element is subject to a rotation, i.e. when the rotatable element transmits a torque between the outer rim and the hub, both, the inner portion and the outer portion may be subject to a well-defined elastic and detectable deformation that can be simultaneously detected and/or quantitatively measured by a first sensor attached to the inner portion and by a second sensor attached to the outer portion.

According to another example at least one of the at least two spokes is configured to elastically deform when a torque is transmitted between the hub and the rim. It is of particular benefit, when the elastically deformable spoke comprises a portion of reduced cross-section compared to other portions of the respective spoke. At a region of reduced cross-section the spoke may exhibit a well-defined elastic deformation behavior as a torque is transmitted between the outer rim and the hub.

According to another example the at least one sensor comprises at least one of a quantum tunneling composite (QTC), a force-sensing sensor and a strain gauge integrated into the rotatable element or adhesively attached to a portion of the rotatable element. The at least one sensor may be embedded in the rotatable element, e.g. in at least one of the at least two spokes of the rotatable element. In other embodiments the sensor is adhesively attached to an outside surface of the rotatable element, e.g. to an outside surface of at least one of the at least two spokes.

When implemented as a QTC sensor the respective sensor comprises a composite material of metals and a non-conducting elastomeric binder. The QTC sensor that can be used as a pressure sensor. The working principle of QTCs uses the so-called quantum tunneling. Where no pressure is applied to the QTC sensor the conductive elements are too far apart to conduct electricity. When a pressure is applied, the conductive elements move closer and electrons can tunnel through the non-conducting elastomeric binder or insulator. This effect is far more pronounced than would be expected from classical, i.e. non-quantum effects alone. Classical electrical resistance is linear, i.e. proportional to a distance between conductive elements while quantum tunneling is exponential with decreasing distance between conductive elements, allowing the resistance to change by a factor of up to $10^{12}$ between pressured and unpressured states.

When implemented as a force sensing resistor the sensor may comprise a material whose electric resistance changes when a force or pressure is applied. The force sensing resistor may comprise a conductive polymer that changes resistance in a predictable manner following application of force to its surface. They are typically supplied as a polymer sheet or ink that can be applied by screen printing. A pressure sensing film consists of both electrically conducting and non-conducting particles that are suspended in a matrix. The particles typically comprise an average size in the sub-micrometer range. Applying a force to the surface of the sensing film causes particles to touch the conducting electrodes, changing the resistance of the film.

With all resistive-based sensors, force sensing resistors require a relatively simple interface and can operate satisfactorily in moderate hostile environments. Compared to other force sensors, the advantages of force sensing resistors are their limited size. Typically, they exhibit a thickness of less than 0.5 mm. Force sensing resistors can be further produced and manufactured with moderate and low costs. They further exhibit a good shock resistance. Electrical signals obtainable from force sensing resistors may be subject to comparatively large tolerances and the measurement precision of such force sensing resistors may be somewhat limited. For detecting variations of a torque transmission across the rotatable element that are induced by a ratchet mechanism that is rotationally coupled or rotationally connected to the rotatable element, the precision and reliability of such force sensing resistors will be sufficient.

When implemented as a strain gauge the sensor of the rotation sensor is configured to measure a strain on or across the rotatable element. The most common type of strain gauges consist of an insulating flexible backing which supports a metallic foil pattern. The strain gauge is attached to the rotatable element by a suitable adhesive, such as cyanoacrylate. As the rotatable element or a portion thereof is subject to a mechanical deformation the foil of the strain gauge is deformed causing its electrical resistance to change. This change in electrical resistance is measureable by an electric circuit, such as a Wheatstone bridge. When the electrical conductor is stretched within the limits of its elasticity its electrical resistance typically increases. Conversely, when the conductor is compressed the electrical resistance may decrease. From the measured electrical resistance of the strain gauge, the amount of induced stress or strain can be inferred.

When implemented as a sensor configured to measure or to detect mechanical strain across the rotatable element at least one or several strain gauges may be attached to the portion of at least one of the at least two spokes exhibiting a reduced cross-section. Here, a first strain gauge may be adhesively attached to one side edge of the spoke. A second strain gauge may be attached to a second side edge of the same spoke. Hence, a first strain gauge may be attached to one side of a spoke a second strain gauge may be attached to an oppositely located side of the same spoke. As the spoke will be subject to a mechanical deformation one of the strain gauges will be subject to stretching whereas the other strain gauge will be subject to compression. In this way, a mechanical deformation of a spoke can be measured redundant. This increases the reliability, failure safety and precision of the rotation sensor.

According to another example the rotatable element comprises at least one ratchet feature configured to periodically engage with at least one counter-ratchet feature when the rotatable element is subject to a rotation relative to the counter-ratchet feature. In this example the rotatable element constitutes or belongs to the ratchet mechanism. The ratchet feature may comprise a toothed structure and the counter-ratchet feature may comprise at least one pawl or detent to engage with the toothed structure of the ratchet feature. In this way, a varying braking effect is applicable to the rotatable element as the rotatable element is subject to the counter-ratchet feature. Implementing the rotatable element itself as a component of a ratchet mechanism enables a rather direct measurement of the variations of the torque across a rotatable element that is applied through the ratchet engagement of the at least one ratchet feature and the at least one counter-ratchet feature. In a further In another example the rotatable element comprises at least one counter-ratchet feature configured to periodically engage with at least one ratchet feature when the rotatable element is subject to a rotation relative to the counter-ratchet feature. In this example the rotatable element constitutes or belongs to the ratchet mechanism and forms a counter-ratchet feature. The counter-ratchet feature may comprise at least one pawl or detent to engage with the toothed structure of the ratchet feature.

According to a further example the processor is configured to detect a temporal variation of an amplitude of the sensor output. The sensor output is provided in form of an electrical signal. By detecting a temporal variation and hence by constantly monitoring the output of the sensor variations of a torque transmitted between the outer rim and the hub can be precisely detected. Every time the sensor output exhibits a positive or negative peak this is an indication, that a ratchet feature of the ratchet mechanism has passed a counter-ratchet feature of the ratchet mechanism. Since the number of ratchet features and counter-ratchet features of the ratchet mechanism is known to the processor and since a full revolution of the rotatable element is assigned with a fixed number of teeth of the ratchet feature the processor is configured to count a number of consecutive peaks or variations of the transmitted torque. As a counted number of torque variations equals the total number of teeth of the ratchet feature this is a clear indication that the rotatable element has been subject to a full revolution relative to the counter-ratchet feature.

In another aspect the disclosure relates to an add-on device for attachment to an injection device. The injection device comprises at least a housing, a trigger, a dial member and an expelling mechanism. The add-on device comprises a body configured for attachment to the dial member and a rotation sensor as described above. Here, the rotatable element of the rotation sensor is rotationally lockable or is rotationally locked to one of the dial member or to one of the housing and the trigger. The rotatable element is rotatable relative to the other one of the dial member or to one of the housing and the trigger via a ratchet mechanism. The ratchet mechanism may belong to the add-on device. In another example the ratchet mechanism is implemented in the expelling or dose setting mechanism of the injection device. However, a variation of an angular momentum can be equally measured at the dial member that is rotationally coupled or rotationally connected to the ratchet mechanism of the injection device.

Insofar, the rotation sensor and the ratchet mechanism may be located both in the add-on device. In another example the rotation sensor is located inside and provided by the add-on device whereas the ratchet mechanism is provided in or on the injection device.

In another aspect the disclosure also relates to an injection device for setting and expelling of a dose of a medicament. The injection device comprises a housing, a trigger to initiate and/or to control expelling of the dose, a dial member rotatable relative to the housing for setting of the dose and a ratchet mechanism. The ratchet mechanism is typically rotationally connected or rotationally coupled to the dial member. The injection device further comprises a rotation sensor as described above. Here, the rotatable element of the rotation sensor is rotationally locked to one of the dial member and the housing. The rotatable element is rotatable relative to the other one of the dial member and the housing via the ratchet mechanism.

In another aspect the disclosure relates to a method of detected and/or quantitatively measuring a rotation of a rotatable element of an injection device or of an add-on device that is configured for attachment to such an injection device. The method comprises the steps of inducing a torque to a rotatable element, wherein the rotatable element is in mechanical engagement with a ratchet mechanism. In a subsequent step at least one of a mechanical force, a mechanical pressure or a mechanical strain is measured at a portion of the rotatable element by at least one sensor attached to the rotatable element. In a subsequent step, an output of the sensor is processed by a processor that is configured to calculate an angle of rotation of the rotatable element on the basis of the output of the at least one sensor.

Typically, the method is conductible by a rotation sensor as described above, which rotation sensor may be implemented in an add-on device for attachment to an injection device or which rotation sensor may be implemented in an injection device directly.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu- Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39), des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by $\alpha$, $\delta$, $\epsilon$, $\gamma$, and $\mu$. The type of heavy chain present defines the isotype of antibody; these chains are found in IgA, IgD, IgE, IgG, and IgM antibodies, respectively.

Distinct heavy chains differ in size and composition; $\alpha$ and $\gamma$ contain approximately 450 amino acids and $\delta$ approximately 500 amino acids, while $\mu$ and $\epsilon$ have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains $\gamma$, $\alpha$ and $\delta$ have a constant region composed of three tandem Ig domains, and a hinge region for added flexibility; heavy chains $\mu$ and $\epsilon$ have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by $\lambda$ and $\kappa$. A light chain has two successive domains: one constant domain (CL) and one variable domain (VL). The approximate length of a light chain is 211 to 217 amino acids. Each antibody contains two light chains that are always identical; only one type of light chain, $\kappa$ or $\lambda$, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure. Further, it is to be noted, that any reference numerals used in the appended claims are not to be construed as limiting the scope of the disclosure.

BRIEF DESCRIPTION OF THE FIGURES

In the following, numerous examples of the container and of an injection device will be described in greater detail by making reference to the drawings, in which:

FIG. 5 is a perspective schematic illustration of a rotation sensor comprising a rotatable element and a counter-ratchet feature, FIG. 6 is an isolated partial illustration of another example of a rotatable element, FIG. 7 is a partial view of a rotation sensor comprising a rotatable element and a ratchet mechanism, FIG. 8 is a schematic illustration of a sensor signal as the rotatable element is subject to a rotation, FIG. 9 is a schematic illustration of an elastic deformation as the rotatable element is subject to a rotation along a first sense of rotation, FIG. 10 is a schematic illustration of the rotatable element when a torque is absent, FIG. 11 is a schematic illustration of an elastic deformation of the rotatable element when it is subject to a rotation along a second sense of rotation, FIG. 12 is a flowchart of a method of determining or detecting a rotation and FIG. 13 is a schematic illustration of a measurement circuit connected to a sensor of the rotation sensor.

DETAILED DESCRIPTION

Figure 1:
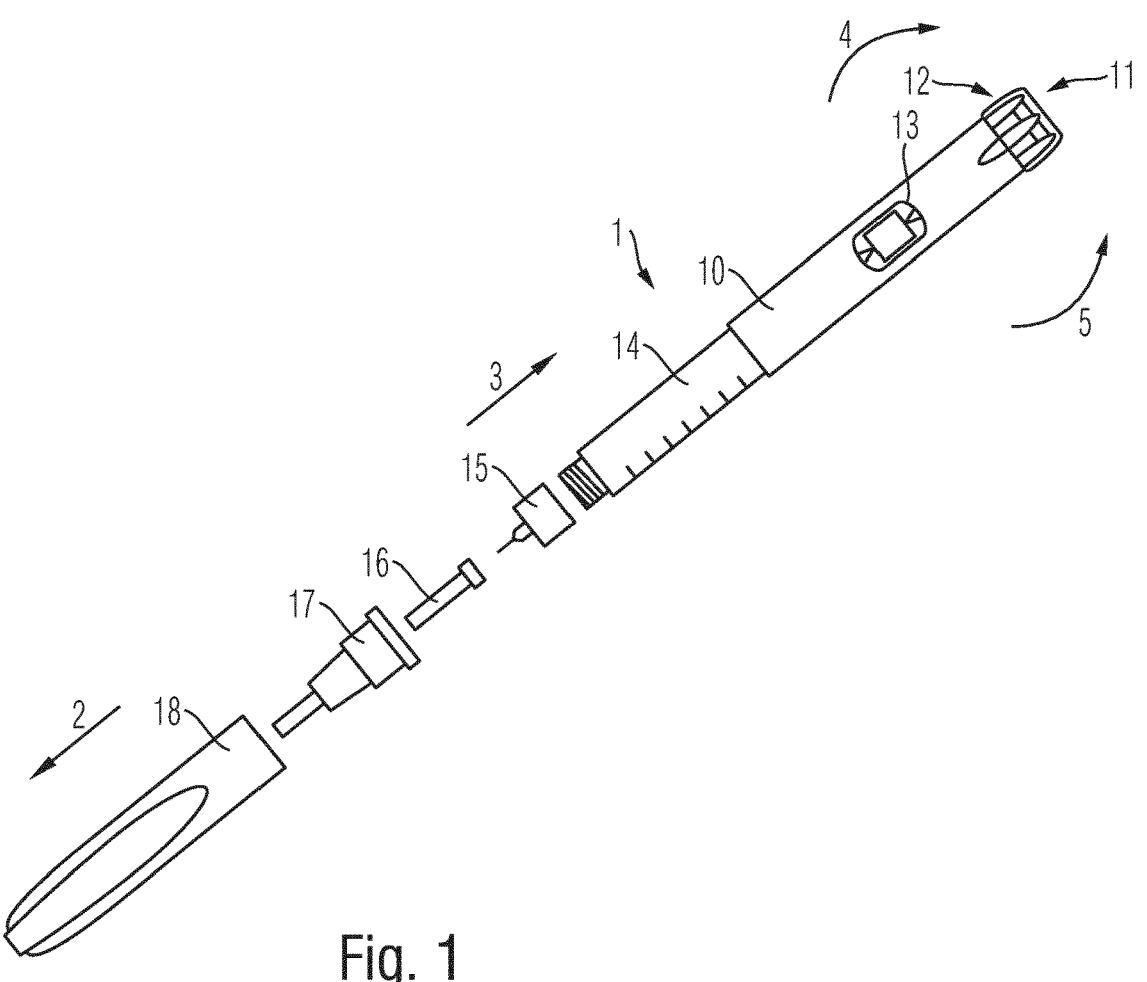
FIG. 1 shows an example of an injection device.
Figure 2:
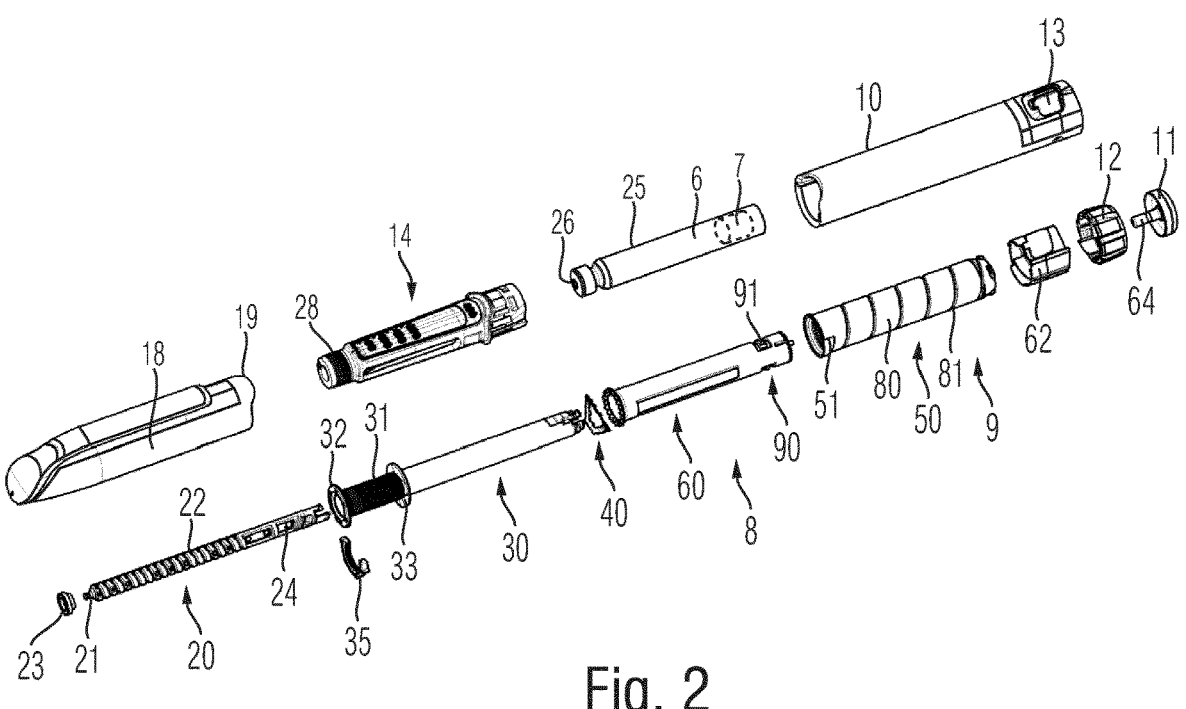
FIG. 2 shows the injection device of FIG. 1 in an exploded perspective view.

The injection device 1 as shown in FIGS. 1 and 2 is a pre-filled disposable injection device that comprises a housing 10 to which an injection needle 15 can be affixed. The injection needle 15 is protected by an inner needle cap 16 and either an outer needle cap 17 or a protective cap 18 that is configured to enclose and to protect a distal section of the housing 10 of the injection device 1. The housing 10 may comprise and form a main housing part configured to accommodate a drive mechanism 8 as shown in FIG. 2. The injection device 1 may further comprise a distal housing component denoted as cartridge holder 14. The cartridge holder 14 may be permanently or releasably connected to the main housing 10. The cartridge holder 14 is typically configured to accommodate a cartridge 6 that is filled with a liquid medicament. The cartridge 6 comprises a cylindrically-shaped or tubular-shaped barrel 25 sealed in proximal direction 3 by means of a bung 7 located inside the barrel 25. The bung 7 is displaceable relative to the barrel 25 of the cartridge 6 in a distal direction 2 by means of a piston rod 20. A distal end of the cartridge 6 is sealed by a pierceable seal 26 configured as a septum and being pierceable by a proximally directed tipped end of the injection needle 15. The cartridge holder 14 comprises a threaded socket 28 at its distal end to threadedly engage with a correspondingly threaded portion of the injection needle 15. By attaching the injection needle 15 to the distal end of the cartridge holder 14 the seal 26 of the cartridge 6 is penetrated thereby establishing a fluid transferring access to the interior of the cartridge 6.

When the injection device 1 is configured to administer e.g. human insulin, the dosage set by a dose dial 12 at a proximal end of the injection device 1 may be displayed in so-called international units (IU, wherein 1 IU is the biological equivalent of about 45.5 µg of pure crystalline insulin (1/22 mg). The dose dial 12 may comprise or may form a dose dial.

As shown further in FIGS. 1 and 2, the housing 10 comprises a dosage window 13 that may be in the form of an aperture in the housing 10. The dosage window 13 permits a user to view a limited portion of a number sleeve 80 that is configured to move when the dose dial 12 is turned, to provide a visual indication of a currently set dose. The dose dial 12 is rotated on a helical path with respect to the housing 10 when turned during setting and/or dispensing or expelling of a dose.

The injection device 1 may be configured so that turning the dosage knob 12 causes a mechanical click sound to provide acoustical feedback to a user. The number sleeve 80 mechanically interacts with a piston in the insulin cartridge 6. When the needle 15 is stuck into a skin portion of a patient, and when the trigger 11 or injection button is pushed, the insulin dose displayed in display window 13 will be ejected from injection device 1. When the needle 15 of the injection device 1 remains for a certain time in the skin portion after the trigger 11 is pushed, a high percentage of the dose is actually injected into the patient's body. Ejection of an insulin dose may also cause a mechanical click sound, which is however different from the sounds produced when using the dose dial 12.

In this embodiment, during delivery of the insulin dose, the dose dial 12 is turned to its initial position in an axial movement, that is to say without rotation, while the number sleeve 80 is rotated to return to its initial position, e.g. to display a dose of zero units.

The injection device 1 may be used for several injection processes until either the cartridge 6 is empty or the expiration date of the medicament in the injection device 1 (e.g. 28 days after the first use) is reached.

Furthermore, before using injection device 1 for the first time, it may be necessary to perform a so-called "prime shot" to remove air from the cartridge 6 and the needle 15, for instance by selecting two units of the medicament and pressing trigger 11 while holding the injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user.

An example of the drive mechanism 8 is illustrated in more detail in FIG. 2. It comprises numerous mechanically interacting components. A flange like support of the housing 10 comprises a threaded axial through opening threadedly engaged with a first thread or distal thread 22 of the piston rod 20. The distal end of the piston rod 20 comprises a bearing 21 on which a pressure foot 23 is free to rotate with the longitudinal axis of the piston rod 20 as an axis of rotation. The pressure foot 23 is configured to axially abut against a proximally facing thrust receiving face of the bung 7 of the cartridge 6. During a dispensing action the piston rod 20 rotates relative to the housing 10 thereby experiencing a distally directed advancing motion relative to the housing 10 and hence relative to the barrel 25 of the cartridge 6. As a consequence, the bung 7 of the cartridge 6 is displaced in distal direction 2 by a well-defined distance due to the threaded engagement of the piston rod 20 with the housing 10.

The piston rod 20 is further provided with a second thread 24 at its proximal end. The distal thread 22 and the proximal thread 24 are oppositely handed.

There is further provided a drive sleeve 30 having a hollow interior to receive the piston rod 20. The drive sleeve 30 comprises an inner thread threadedly engaged with the proximal thread 24 of the piston rod 20. Moreover, the drive sleeve 30 comprises an outer threaded section 31 at its distal end. The threaded section 31 is axially confined between a distal flange portion 32 and another flange portion 33 located at a predefined axial distance from the distal flange portion 32.

Between the two flange portions 32, 33 there is provided a last dose limiter 35 in form of a semi-circular nut having an internal thread mating the threaded section 31 of the drive sleeve 30.

The last dose limiter 35 further comprises a radial recess or protrusion at its outer circumference to engage with a complementary-shaped recess or protrusion at an inside of the sidewall of the housing 10. In this way the last dose limiter 35 is splined to the housing 10. A rotation of the drive sleeve 30 in a dose incrementing direction 4 or clockwise direction during consecutive dose setting procedures leads to an accumulative axial displacement of the last dose limiter 35 relative to the drive sleeve 30. There is further provided an annular spring 40 that is in axial abutment with a proximally facing surface of the flange portion 33. More- over, there is provided a tubular-shaped clutch 60. At a first end the clutch 60 is provided with a series of circumferen- tially directed saw teeth. Towards a second opposite end of the clutch 60 there is located a radially inwardly directed flange.

Furthermore, there is provided a dose dial sleeve also denoted as number sleeve 80. The number sleeve 80 is provided outside of the spring 40 and the clutch 60 and is located radially inward of the housing 10. A helical groove 81 is provided about an outer surface of the number sleeve 80. The housing 10 is provided with the dosage window 13 through which a part of the outer surface of the number 80 can be seen. The housing 10 is further provided with a helical rib at an inside sidewall portion of an insert piece 62, which helical rib is to be seated in the helical groove 81 of the number sleeve 80. The tubular shaped insert piece 62 is inserted into the proximal end of the housing 10. It is rotationally and axially fixed to the housing 10. There are provided first and second stops on the housing 10 to limit a dose setting procedure during which the number sleeve 80 is rotated in a helical motion relative to the housing 10. As will be explained below in greater detail, at least one of the stops is provided by a preselector stop feature 71 provided on a preselector 70.

The dose dial 12 in form of a dose dial grip is disposed about an outer surface of the proximal end of the number sleeve 80. An outer diameter of the dose dial 12 typically corresponds to and matches with the outer diameter of the housing 10. The dose dial 12 is secured to the number 80 to prevent relative movement there between. The dose dial 12 is provided with a central opening.

The trigger 11, also denoted as dose button is substantially T-shaped. It is provided at a proximal end of the injection device 10. A stem 64 of the trigger 11 extends through the opening in the dose dial 12, through an inner diameter of extensions of the drive sleeve 30 and into a receiving recess at the proximal end of the piston rod 20. The stem 64 is retained for limited axial movement in the drive sleeve 30 and against rotation with respect thereto. A head of the trigger 11 is generally circular. The trigger side wall or skirt extends from a periphery of the head and is further adapted to be seated in a proximally accessible annular recess of the dose dial 12.

To dial a dose a user rotates the dose dial 12. With the spring 40 also acting as a clicker and the clutch 60 engaged, the drive sleeve 30, the spring or clicker 40, the clutch 60 and the number sleeve 80 rotate with the dose dial 12.

Audible and tactile feedback of the dose being dialed is provided by the spring 40 and by the clutch 60. Torque is transmitted through saw teeth between the spring 40 and the clutch 60. The helical groove 81 on the number sleeve 80 and a helical groove in the drive sleeve 30 have the same lead. This allows the number sleeve 80 to extend from the housing 10 and the drive sleeve 30 to climb the piston rod 20 at the same rate. At a limit of travel a radial stop on the number sleeve 80 engages either with a first stop or a second stop provided on the housing 10 to prevent further move- ment in a first sense of rotation, e.g. in a dose incrementing direction 4. Rotation of the piston rod 20 is prevented due to the opposing directions of the overall and driven threads on the piston rod 20.

The last dose limiter 35 keyed to the housing 10 is advanced along the threaded section 31 by the rotation of the drive sleeve 30. When a final dose dispensed position is reached, a radial stop formed on a surface of the last dose limiter 35 abuts a radial stop on the flange portion 33 of the drive sleeve 30, preventing both, the last dose limiter 35 and the drive sleeve 30 from rotating further.

Should a user inadvertently dial beyond the desired dos- age, the injection device 1, configured as a pen-injector allows the dosage to be dialed down without dispense of the medicament from the cartridge 6. For this the dose dial 12 is simply counter-rotated. This causes the system to act in reverse. A flexible arm of the spring or clicker 40 then acts as a ratchet preventing the spring 40 from rotating. The torque transmitted through the clutch 60 causes the saw teeth to ride over one another to create the clicks corresponding to dialed dose reduction. Typically, the saw teeth are so dis- posed that a circumferential extent of each saw tooth cor- responds to a unit dose. Here, the clutch may serve as a ratchet mechanism.

As an alternative or in addition the ratchet mechanism 90 may comprise at least one ratchet feature 91, such as a flexible arm on the sidewall of the tubular-shaped clutch 60. The at least one ratchet feature 91 may comprise a radially outwardly extending protrusion e.g. on a free end of the flexible arm. The protrusion is configured to engage with a correspondingly shaped counter ratchet structure on an inside of the number sleeve 80. The inside of the number sleeve 80 may comprise longitudinally shaped grooves or protrusions featuring a saw-tooth profile.

During dialing or setting of a dose the ratchet mechanism 90 allows and supports a rotation of the number sleeve 80 relative to the clutch 60 along a second sense of rotation 5, which rotation is accompanied by a regular clicking of the flexible arm of the clutch 60. An angular momentum applied to the number sleeve 80 along the first sense of rotation for is unalterably transferred to the clutch 60. Here, the mutually corresponding ratchet features of the ratchet mechanism 90 provide a torque transmission from the number sleeve 80 to the clutch 60.

When the desired dose has been dialed the user may simply dispense the set dose by depressing the trigger 11. This displaces the clutch 60 axially with respect to the number sleeve 80 causing dog teeth thereof to disengage. However, the clutch 60 remains keyed in rotation to the drive sleeve 30. The number sleeve 80 and the dose dial 12 are now free to rotate in accordance with the helical groove 81.

The axial movement deforms the flexible arm of the spring 40 to ensure the saw teeth cannot be overhauled during dispense. This prevents the drive sleeve 30 from rotating with respect to the housing 10 though it is still free to move axially with respect thereto. The deformation is subsequently used to urge the spring 40 and the clutch 60 back along the drive sleeve 30 to restore the connection between the clutch 60 and the number sleeve 80 when the distally directed dispensing pressure is removed from the trigger 11.

The longitudinal axial movement of the drive sleeve 30 causes the piston rod 20 to rotate through the through opening of the support of the housing 10, thereby to advance the bung 7 in the cartridge 6. Once the dialed dose has been dispensed, the number sleeve 80 is prevented from further rotation by contact of at least one stop extending from the dose dial 12 with at least one corresponding stop of the housing 10. A zero dose position may be determined by the abutment of one of axially extending edges or stops of the number sleeve 80 with at least one or several corresponding stops of the housing 10.

The expelling mechanism or drive mechanism 8 as described above is only exemplary for one of a plurality of differently configured drive mechanisms that are generally implementable in a disposable pen-injector. The drive mechanism as described above is explained in more detail e.g. in WO2004/078239A1, WO 2004/078240A1 or WO 2004/078241A1 the entirety of which being incorporated herein by reference.

The dose setting mechanism 9 as illustrated in FIG. 2 comprises at least the dose dial 12 and the number sleeve 80. As the dose dial 12 is rotated during and for setting of a dose the number sleeve 80 starts to rotate relative to the housing along a helical path as defined by the threaded engagement of its outer thread or helical groove 81 with a correspondingly shaped threaded section at the inside surface of the housing.

During dose setting and when the drive mechanism 8 or the dose setting mechanism 9 is in the dose setting mode the drive sleeve 30 rotates in unison with the dose dial 12 and with the number sleeve 80. The drive sleeve 30 is threadedly engaged with the piston rod 20, which during dose setting is stationary with regard to the housing 10. Accordingly, the drive sleeve 30 is subject to a screwing or helical motion during dose setting. The drive sleeve 30 starts to travel in proximal direction as the dose dial is rotated in a first sense or rotation or in a dose incrementing direction 4, e.g. in a clockwise direction. For adjusting of or correcting a size of a dose the dose dial 12 is rotatable in an opposite second sense of rotation, hence in a dose decrementing direction 5, e.g. counterclockwise.

The working principle of the rotation sensor 200 is illustrated in FIGS. 5-11. The rotation sensor 200 comprises a rotatable element 201. The rotatable element 201 may comprise a wheel 202. The rotation sensor 200 further comprises at least one sensor 220, 222, 224 as indicated in FIG. 5. There may be provided a plurality of sensors of equal type or of different type connected to or embedded in the rotatable element 201. The sensors 220, 222, 224 comprise at least one of a QTC, a force-sensing resistor and a strain gauge. By having several sensors 220, 222, 224 applied to different portions of the rotatable element 201, a failure safe and redundant measurement of a torque transmitted between an outer rim 208 and a hub 210 of the rotatable element 201 can be simultaneously detected by several sensors 220, 222, 224. In principle, only one sensor 220, 222, 224 will be generally sufficient to detect a variation of a torque transmission between the outer rim 208 and the hub 210.

The rotatable element 201 is in mechanical engagement with a ratchet mechanism 90, 190. A ratchet mechanism 90 may be implemented in the injection device 1. A ratchet mechanism 190 may be implemented in an add-on device 100 as described in connection with FIGS. 3 and 4.

In the illustration of FIGS. 5 and 6 the rotatable element 201 of the rotation sensor 200 coincides with a component of a ratchet mechanism 190. For this the rotatable element 201 comprises at least one ratchet feature 212. There may be provided a plurality of ratchet features 212 on the outer rim 208 of the rotatable element 201. The ratchet features 212 may be equidistantly arranged on the outside circumference of the rotatable element 201. They may be located on a radially outwardly facing side edge of the wheel 202. The various ratchet features 212 may be of equal or identical geometry. Each one of the ratchet features 212 may comprise or may constitute a ratchet tooth.

So each ratchet feature 212 comprises a beveled edge 214 facing in a first sense of rotation 4. The ratchet features 212 comprise a flank 216 facing in a second sense of rotation 5. The first and the second senses of rotation are opposite to each other. As illustrated in FIG. 5, the beveled edge 214 faces in a clockwise direction whereas the flange 216 faces in a counter-clockwise direction. The ratchet feature 212 may exhibit a symmetric geometry. Hence, the beveled edge 214 and the flank 216 may be symmetric to each other as seen in the circumferential or tangential direction of the wheel 202. In other examples, the shape and/or the slope of the beveled edge 214 may differ from a shape and/or slope of a flank 216.

The ratchet mechanism 190 may support a rotation of the rotatable element 201 along the first sense of rotation 4 and along a second sense of rotation 5. The ratchet mechanism 190 may be implemented to enable a rotation of the rotatable element 209 relative to a counter-ratchet feature 240 only along one of the first sense of rotation 4 and the second sense of rotation 5, wherein a rotation along the other one of the first sense of rotation 4 and the second sense of rotation 5 is prevented or inhibited.

Moreover, when supporting and allowing a rotation along the first sense of rotation 4 and a rotation along the second sense of rotation 5 the ratchet mechanism 190 may be configured to provide variable mechanical resistance or a varying braking effect of different magnitude. The magnitude of a braking effect induced by the counter-ratchet feature 240 on the rotatable element 201 may depend on the sense of rotation. A torque required to rotate the rotatable element 201 along the first sense of rotation 4 may differ to a torque required to rotate the rotatable element 201 along the second sense of rotation 5 relative to the counter-ratchet feature 240. In the present illustration the rotatable element 201 is rotatable relative to a counter-ratchet feature 240. The counter-ratchet feature 240 may be fixed or connected to a housing 10 of an injection device 1. The counter-ratchet feature 240 may be also connected to a housing 101 of an add-on device 100. Likewise, it is conceivable, that the rotatable element 201 is rotationally locked to a respective housing 10, 101 whereas the counter-ratchet feature 240 is subject to a rotation, e.g. during a dose setting or dose expelling procedure conducted by the injection device 1.

The counter-ratchet feature 240 comprises a flexible arm 241 comprising at least one protrusion 242 configured to mechanically engage with the at least one ratchet feature 212 of the rotatable element 201. The protrusion 242 comprises a beveled edge 244 and a flank 246. The beveled edge 244 may face towards the second sense of rotation 5 whereas the flank 246 is located at an opposite edge of the protrusion 242. The flank 246 may face towards the first sense of rotation 4.

The beveled edges 240, 244 of the rotatable element 201 and the counter-ratchet feature 240 are complementary-shaped. The same applies to the mutually corresponding flanks 216, 246. In this way the rotatable element 201 is rotatable relative to the counter-ratchet feature 240 while the at least one ratchet feature 212 periodically engages with a correspondingly-shaped protrusion 242 of the counter-ratchet feature 240. In typical implementations the counter-ratchet feature 240 comprises only one or a limited number of radially inwardly extending protrusions 242 and the rotatable element 201 comprises a toothed structure with a number of consecutively and equidistantly arranged teeth or ratchet features 212 on a radial outside facing edge of the outer rim 208.

The mechanical engagement of the ratchet feature 212 or of the ratchet features 212 with the counter-ratchet feature 240 induce a varying torque across the rotatable element 201. The hub 210 of the rotatable element 201 is rotationally fixed to a component of the injection device 1 or of the add-on device 100. As the rotatable element 201 is subject to a rotation, e.g. during a dose setting operation or dose expelling operation a torque is transmitted between the outer rim 208 and the centrally located hub 210. Since the ratchet mechanism 190 induces a variation of the torque across the rotatable element the various sensors 220, 222, 224 are configured to measure such a variation of the torque transmission.

The processor 112 connected to the sensors 220, 222, 224 is implemented to measure a temporal variation of the transmitted torque. Any temporal variation of the transmitted torque detected by the at least one sensor 220, 222, 224 is a direct indication that a ratchet feature 212 of the rotatable element 201 has passed a correspondingly-shaped counter-ratchet feature 240. Since the number and the arrangement of the ratchet features 212 and the counter-ratchet features 240 is known the processor 112 is enabled to determine an angle of rotation by counting the number of detectable variations of the torque transmitted between the outer rim 208 and the hub 210.

The rotatable element 201 as illustrated in FIGS. 5, 6 and 9-11 comprises numerous spokes, 204, 206. The spokes 204, 206 form a mechanical connection between the outer rim 208 and the hub 210. By way of the spokes 204, 206 a torque can be transmitted between the outer rim 208 and the hub 210. There may be provided numerous spokes, such as two spokes, three spokes, four or even more spokes 204, 206. With a rather limited number of spokes the various spokes may be rather susceptible to mechanical deformation as a torque is transferred between the outer rim 208 and the hub 210.

Typically, the spokes 204, 206 are typically equidistantly arranged along the inner circumference of the outer rim 208 or along the outer circumference of the hub 210. The spokes 204, 206 are configured to deform elastically as a torque is transmitted between the outer rim 208 and the hub 210. By arranging the at least one sensor 220, 222, 224 to at least one of the spokes 204, 206 the degree of elastic deformation of the respective spoke 204, 206 can be detected and/or quantitatively determined. In order to have a well-defined deformation behavior at least in a portion of the spokes the individual spokes 204, 206 may comprise a portion of reduced cross-section.

Figures 9, 10, 11, 12, 13:
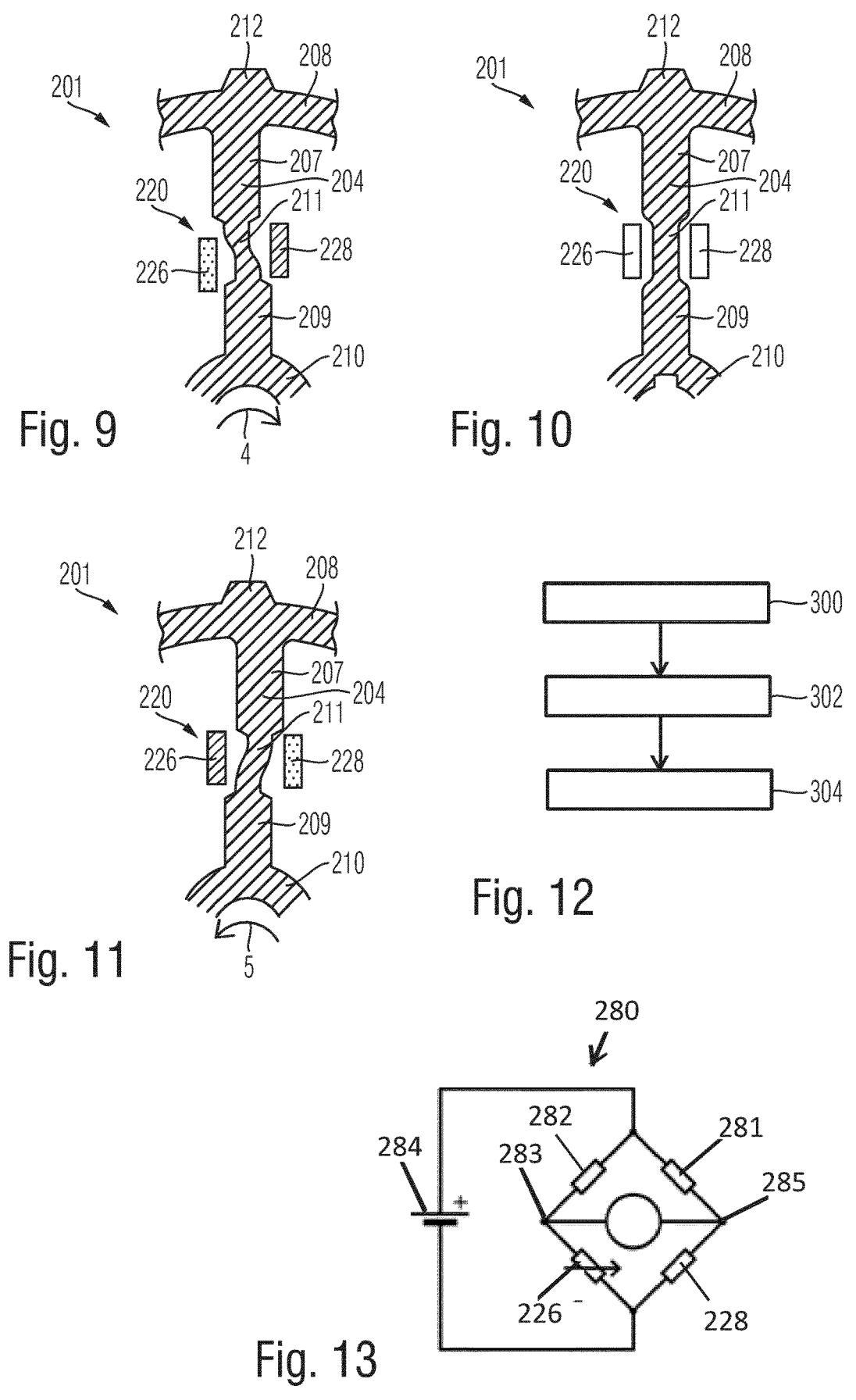

As illustrated in greater detail in FIG. 9 the spoke 204 comprises an outer portion 207 connected to the outer rim 208. The spoke 204 further comprises an inner portion 209 connected to the hub 210. The spoke 204 further comprises a middle portion 211 located between the outer portion 207 and the inner portion 209. Compared to the cross-sections of the outer portion 207 and the inner portion 209 the middle portion 211 comprises a smaller or a reduced cross-section. In this way and as indicated in FIGS. 9 and 11 the middle portion 211 is particularly susceptible to mechanical deformation. As indicated, the middle portion 211 is subject to a geometric deformation as a torque is applied to the hub 210 along a first sense of rotation 4.

As indicated and since the outer rim 208 is in ratchet engagement with the stationary counter-ratchet feature 240 the outer rim 208 experiences a respective mechanical resistance against a rotation along the first sense of rotation 4. Here, the counter-ratchet feature 240 may be arranged at or in a housing 101 of an add-on device 100. Alternatively, the counter-ratchet feature 240 may be provided or located on or in the housing 10 of the injection device 1.

Accordingly and depending on the varying magnitude of a braking effect induced by the mutually corresponding ratchet feature 212 and counter-ratchet feature 240 the middle portion 211 of the spoke 204 is subject to a regular mechanical deformation as the rotatable element 201 is rotated along the first sense of rotation 4. At least one sensor 220 is connected or attached to the middle portion 211. In the illustrated example of FIGS. 9, 10 and 11 the sensor 220 comprises two strain gauges 226, 228. A first strain gauge 226 is attached to a side of the spoke 204 facing in the second sense of rotation 5. A second strain gauge 228 is arranged at a side of the spoke 204 facing in the first sense of rotation 4. In other words, the two strain gauges 226, 228 are located on opposite sides of the spoke 204.

As indicated further in FIGS. 9-11 the strain gauges 226, 228 are located on opposite sides of the middle portion 211 of the spoke 204. As a torque is applied to the hub 210 along the first direction 4 the outer portion 207 is subject to a displacement relative to the inner portion 209 along the second sense of rotation 5. Accordingly, the strain gauge 226 is subject to compression whereas the strain gauge 228 is subject to a stretching. In another scenario, wherein the hub 210 is subject to a torque along the second sense of rotation 5 the rim 208 is subject to a circumferential or tangential displacement along the first sense of rotation 4 relative to the hub 210. Accordingly and as indicated in FIG. 11 the strain gauge 226 is subject to stretching and the strain gauge 228 is subject to compression.

In a neutral configuration as illustrated in FIG. 10, where no substantial torque is applied to the rotatable element 201 there is no substantial compression or stretching effect to any of the strain gauges 226, 228.

As the rotatable element 201 is rotated either along the first sense of rotation 4 or along the second sense of rotation 5, e.g. during setting of a dose and/or during expelling of a dose of the medicament the middle portion 211 is subject to a repetitive mechanical deformation that is detectable and measurable by the sensor 220. Typically, the degree of mechanical deformation is proportional to a magnitude of a torque transmitted between the rim 208 and hub 210.

In other configurations it is conceivable, that an external torque is applied to the outer rim 208 and is hence transferred radially inwardly from the outer rim 208 to the centrally located hub 210. The middle portion 211 will then be subject to a respective deformation.

The magnitude or degree of deformation directly corresponds to the magnitude of the torque transferred between the outer rim 208 and the hub 210. Since the rotatable element 201 is mechanically or rotationally engaged with the ratchet mechanism 190 the torque transferred between the outer rim 208 and the hub 210 is subject to variations as indicated in FIG. 8. Every time a ratchet feature 212 of the rotatable element 201 passes a counter-ratchet feature 240 the transmitted torque exhibits a detectable drop 262 as indicated in the diagram 260 of FIG. 8. Every detectable peak or drop 262 in the diagram 260 is detectable by the at least one sensor 220, 222, 224 of the rotation sensor 200.

With the example of the strain gauges 226, 228 FIG. 13 illustrates one of a plurality of measurement circuits 280 configured to measure a varying electrical resistance of at least one of the strain gauges 226, 228. The strain gauges 226, 228 are arranged in a Wheatstone bridge circuit as illustrated in FIG. 13. The measurement circuit 280 comprises a first reference resistor 281 and a second reference resistor 282 of known and constant resistance. The resistors 281 and 282 are arranged in parallel. The resistor 282 is connected in series with the strain gauge 226. The resistor 281 is in series with the strain gauge 228. The strain gauges 226, 228 are also connected parallel. Two opposite vertices of the measurement circuit 280 are connected to a current source 284. There is provided a node 283 between the reference resistor 282 and the strain gauge 226. There is provided a further node 285 between the reference resistor 281 and the strain gauge 228. Across the two nodes 283, 285 a voltage can be detected that is directly indicative of the variable resistance of the strain gauge 226 and/or of the strain gauge 228. In this way, the variable electrical resistance of the strain gauges 226, 228 can be detected and quantitatively measured, thus supporting a detection of the peaks or drops 262 in the diagram 260 as the rotatable element 201 is subject to a rotation relative to the counter-ratchet feature 240.

In FIG. 12 a method of measuring a rotation of a rotatable element 201 is indicated. In a first step 300 a torque is induced or applied to the rotatable element when the rotatable element is in mechanical engagement with a ratchet mechanism 90, 190 of an injection device 1 or of an add-on device 100, respectively. Thereafter in a further step 302, a sensor output of at least one sensor 220, 222, 224 is measured. In a further step 304, the measured sensor output is processed by a processor 112. The processor 112 and its electric connection to the at least one sensor 220, 222, 224 is configured to monitor a temporal variation of an amplitude of the sensor output. Temporal variations or particular peaks in the output or output signal of the at least one sensor 220, 222, 224 are indicative that the rotatable element has been rotated by a discrete step, wherein the step size is governed and determined by the geometry and interaction of the ratchet mechanism 90, 190.

When the rotation sensor 200 is implemented into an injection device as illustrated in FIGS. 1 and 2 it may be located on a rotatable element 201, such as a rotatable clutch 60 comprising a clutch sleeve having a flexible ratchet feature 91 that is in ratchet engagement with a number sleeve 80. For setting of a dose the number sleeve 80 is subject to a rotation relative to the clutch 60. Here, the ratchet feature comprising a flexible arm with a radially outwardly extending protrusion is in regular engagement with a correspondingly-shaped counter-ratchet feature provided on an inside sidewall section of the number sleeve 80. During setting of a dose the dial member 12 is in torque-proof engagement with the number sleeve 80. When the dial member 12 is rotated in at least one of the first sense of rotation 4 and the second sense of rotation 5, the ratchet engagement between the number sleeve 80 and the clutch 60 is regularly overhauled. For rotating the dose dial or dose member 12 along the first sense of rotation 4 or along a second sense of rotation 5, e.g. for reducing a size of a dose or for correcting of a dose setting the torque required to rotate the dial member 12 one step further is subject to regular variations due to the ratchet engagement between the number sleeve 80 and the clutch 60.

In principle, any rotatable component arranged in a torque transmission between the clutch 60 and the dose dial 12 may serve as the rotatable element 201 as described above. For instance, the dose dial 12 itself may be configured as the rotatable element 201.

Figure 3:
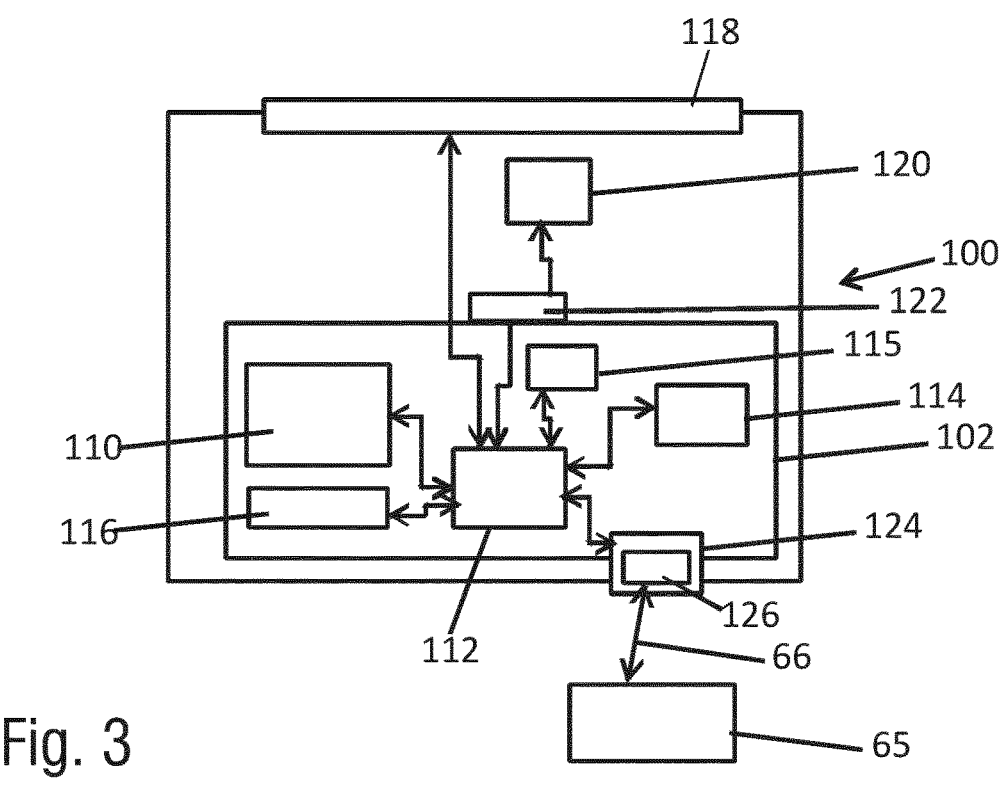
FIG. 3 shows a block diagram of an add-on device.
Figure 4:
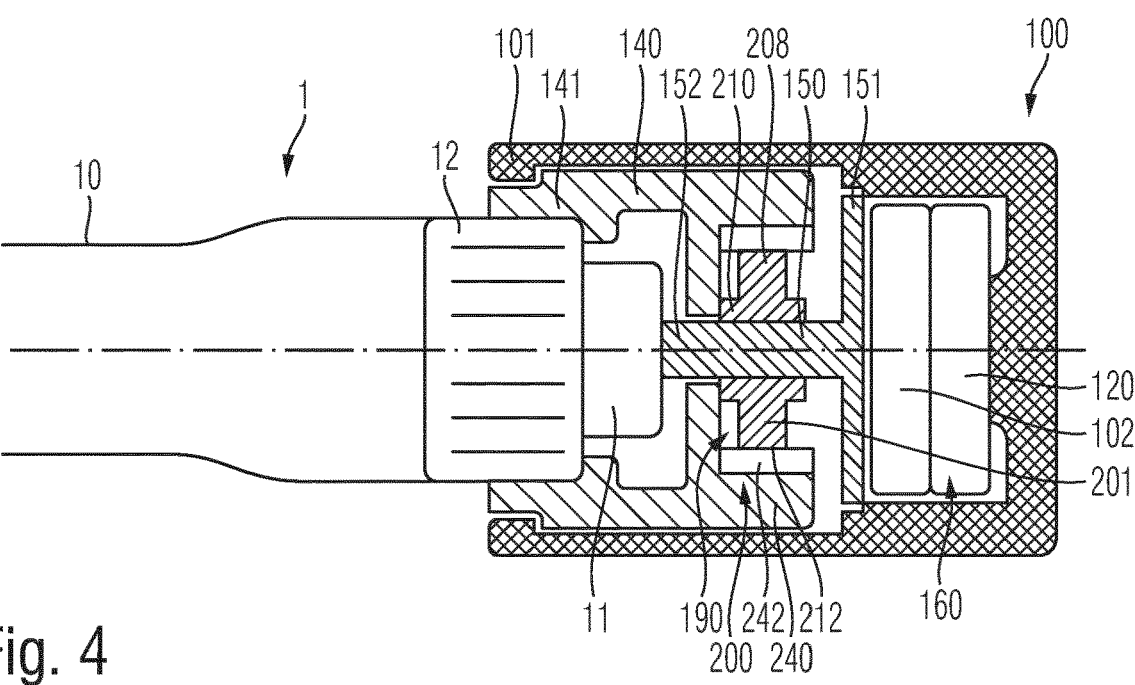
FIG. 4 is a longitudinal cross-section of an add-on device when attached to a proximal end of an injection device.

In FIGS. 3 and 4 an implementation of the rotation sensor 200 in an add-on device 100 is schematically illustrated. Here, the add-on device 100 comprises a housing 101 configured for assembly to a proximal end of a pen-type injection device 1. The add-on device 100 further comprises an insert 140 that is rotationally connected and hence rotationally locked to the housing 101. The insert 140 comprises a skirt 141 configured for a friction fit or a positive locking fit with the rotatable dose dial 12. There is further provided a pressure piece 150 that is rotationally supported inside the housing 101. The pressure piece 150 is free to rotate relative to the housing 101. The pressure piece 150 comprises a disc section 151 and a longitudinal stem 152 extending in longitudinal direction from a radial center of the disc section 151. A free end of the stem 152 facing away from the disc section 151 is rotationally lockable or locked to the trigger 11.

The trigger 11 is rotationally locked to the housing 10 of the injection device 1 at least during one of setting of a dose and dispensing of a dose. By means of the stem 152, which is in axial abutment with the trigger 11, the trigger 11 is depressible in distal direction 2 through the pressure piece 150. The pressure piece 150 is in axial abutment or axial engagement with the housing 101 of the add-on device 100. The housing 101 is axially slidably displaceable relative to the insert 140. While the insert 140 is axially fixed to the dial member 12 the housing 101 can be axially displaced in distal direction 2 relative to the insert 140 for initiating a dose expelling procedure. In this way the trigger 11 is displaceable in distal direction 2 relative to the housing 10 by urging the housing 101 of the add-on device 100 in distal direction 2 relative to the housing 10 of the injection device 1.

The stem 152 is in one of a form fitting engagement and a frictional engagement with the trigger 11. It is hindered to rotate relative to the housing 10 of the injection device 1. The stem 152 intersects a rotatable element 201 of the rotation sensor 200. The stem 152 is rotationally locked to a stem 210 of the rotatable element 201. It may be in a splined engagement with the stem 210. For this at least one of the stem 152 and the bore of the hub 210 comprises a radial protrusion engaged with a correspondingly-shaped radial recess of the other one of the stem 152 and the hub 210.

The housing 101 as illustrated in FIG. 4 further comprises a compartment to receive the electronic components of the add-on device 100. There is provided an accommodation space 160 between the pressure piece 150 and a proximal end face of the housing 101. This accommodation space 160 is configured to receive a printed circuit board 102 provided with the processor 112. The processor 112 is electrically connected to the sensors 220, 222, 224. The accommodation space 160 is further configured to receive a power source 120, such as a button battery.

The rotatable element 201 as illustrated in FIG. 4 is located radially inside a counter-ratchet feature 240 of the insert 140. As the housing 101 of the add-on device 100 is rotated relative to the housing 10 of the injection device, thereby inducing a torque to the dose dial 12 the insert 140 and hence the counter-ratchet feature 240 rotates relative to the rotatable element 201 in accordance to the ratchet mechanism 190 constituted by the ratchet features 212 of the rotatable element 201 and the counter-ratchet feature 240 of the insert 140.

Insofar, the implementation of the rotation sensor 200 in an add-on device 100 as illustrated in FIG. 4 is directly compatible with the illustration of a rotation sensor 200 as shown in FIGS. 5, 6 and any of the FIGS. 9-11.

In FIG. 7 another example of a rotation sensor 200 is illustrated. Here, a rotatable element 201 comprises a rotatable wheel 202 that is only shown in sections in FIG. 7. The wheel 202 comprises numerous regularly or irregularly arranged ratchet features 212. Each ratchet feature represents a tooth of a ratchet mechanism 90. There is further provided a counter-ratchet feature 340 comprising a flexible arm 341 having a radially inwardly extending protrusion 342. The protrusion 342 comprises a beveled edge 344 and a flank 346 on oppositely located circumferential or tangential side edges. The counter-ratchet feature 340 is subject to a repetitive and regular elastic bending as the rotatable element 201 is rotated relative to the counter-ratchet feature 340. As indicated in FIG. 7 the radially outwardly located tips of the ratchet feature 212 are provided with a sensor 224. Here, the sensor 224 may be implemented as a pressure sensor or as a contact sensor configured to detect a mechanical contact between any of the ratchet features 212 with the counter-ratchet feature 340. Electrical signals generated by the at least one or by a plurality of sensors 224 are processed by the processor 112 thus being indicative, that the rotatable element 201 has been rotated relative to the counter-ratchet feature 340 by a discrete step. The step size is governed and determined by the geometry and position of the ratchet features 212.

The rotatable element 201 forms a first component of a ratchet mechanism 90 and the counter ratchet feature 240 forms a second component of the ratchet mechanism 90. The ratchet features 212 of the rotatable element 201 form or constitute teeth of the ratchet mechanism of the first ratchet component. The counter ratchet features 242 of the counter ratchet feature 240 comprises, form or constitute a pawl or a detent configured to engage with the ratchet features 212.

FIG. 3 is a block diagram of an add-on device 100. The add-on device 100 may comprise a data collection device. The add-on device 100 comprises processor 112 including one or more processors, such as a microprocessor, a Digital Signal Processor (DSP), Application Specific Integrated Circuit (ASIC), Field Programmable Gate Array (FPGA) or the like, together with a memory 114. The memory may 114 include a program memory and main memory, which can store software for execution by the processor 112 and data generated during use of the add-on device 100 such as counted pulses, derived dose size, time stamp, etc. A switch 122 connects a power source 120 to the electronic components of the device 100, including a sensor arrangement 110. A display 118 may or may not be present. The sensor arrangement 110 comprises at least a rotation sensor 200 configured for detecting and/or for or quantitatively measuring a rotational movement between the housing 10 and the dose dial 12 of the injection device 1.

The resolution of the sensor arrangement 110 is determined by the design of the injection device 1. A suitable angular resolution of the sensor arrangement 110 may be determined by Equation (1):

$$resolution = \frac{360°}{units\_per\_rotation} \qquad (1)$$

For instance, if one full rotation of the dial member 12 corresponds to a medicament dosage amount of 24 IU, then a suitable resolution for the sensor arrangement 110 would be not more than 15°.

Typically, the angle of rotation of the dose dial 12 or dial ember measured by the rotation sensor 200 is proportional to the amount of medicament expelled. It is not necessary to determine a zero level or an absolute amount of medicament contained in the injection device 1. When the dose dial 12 rotates relative to the housing 10 during expelling of a dose of the medicament the dose actually expelled can be precisely determined and monitored by the add-on device 100. Here, the rotation sensor 200 provides a direct and thus more reliable information about the amount of medicament that is injected compared to data collection devices that determine the amount of medicament that is set, thus being intended to be dispensed.

The add-on device 100 comprises an interface 124 connected to the processor 112. The interface 124 may be a wireless communications interface for communicating with another external device 65, e.g. in form of a portable electronic device, via a wireless network such as Wi-Fi or Bluetooth®, or an interface for a wired communications link, such as a socket for receiving a Universal Series Bus (USB), mini-USB or micro-USB connector. For this, the interface 124 comprises a transceiver 126 configured for transmitting and receiving data. FIG. 3 depicts an example of an injection system in which the add-on device 100 is connected to an external electronic device 65, such as a personal computer 65, via a data connection 66 for data transfer. The data connection 66 may be of wired or wireless type.

For example, the processor 112 may store determined delivered medicament amounts and time stamps for the injections as they are administered by the user and subsequently, transfer that stored data to the external electronic device 65. The device 65 maintains a treatment log and/or forwards treatment history information to a remote location, for instance, for review by a medical professional.

The add-on device 100 or data collection device may be configured to store data such as delivered medicament amounts and time stamps of up to numerous injection events, such as 35 or more injection events. According to a once-daily injection therapy this would be sufficient to store a treatment history of about one month. Data storage is organized in a first-in first-out manner ensuring that most recent injection events are always present in the memory of the data collection device 100. Once transferred to an external electronic device 65 the injection event history in the add-on device 100 will be deleted. Alternatively, the data remains in the add-on device 100 and the oldest data is deleted automatically once new data is stored. This way the log in the data collection device is built up over time during usage and will always comprise the most recent injection events. Alternatively, other configuration could comprise a storage capacity of 70 (twice daily), 100 (three months) or any other suitable number of injection events depending on the therapy requirements and/or the preferences of the user.

In another embodiment, the interface 124 may be configured to transmit information using a wireless communications link and/or the processor 112 may be configured to transmit such information to the external electronic device 65 periodically.

The processor 112 may control the optional display 118 to show the determined medicament dose information, and/or to show an elapsed time since a last medicament dose was delivered. For example, the processor arrangement 112 may cause the display 118 to switch periodically between displaying the most recent determined medicament dosage information and the elapsed time.

The power source 120 may be a battery. The power source 120 may be a coin cell, or multiple coin cells arranged in series or parallel. A timer 115 may be also provided. In addition to, or instead of, switching the add-on device 100 on and off, the switch 122 may be arranged to trigger the timer 115 when engaged and/or disengaged. For example, if the timer 115 is triggered on both engagement or disengagement of the first and second electrical contacts of the switch or both operation and ceasing of operation of the switch 122, then the processor 112 may use the output from the timer 115 to determine a length of time during which the trigger 11 was pressed, for example to determine the duration of an injection.

Alternatively, or additionally, the processor 112 may use the timer 115 to monitor a length of time that has elapsed since an injection was completed, as indicated by a time of disengagement of respective switch components or ceasing of operation of the switch 122. Optionally, the elapsed time may be shown on the display 118. Also optionally, when the switch 122 is next operated, the processor 112 may compare the elapsed time with a predetermined threshold, to determine whether a user may be attempting to administer another injection too soon after a previous injection and, if so, generate an alert such as an audible signal and/or a warning message on the display 118 or via the output 116. The output 160 may be configured to generate an audible sound or to induce a vibration hence to produce a tactile signal, e.g. for alerting the user.

On the other hand, if the elapsed time is very short, it may indicate that the user is administering a medicament amount as a "split dose", and the processor 112 may store information indicating that a dosage was delivered in that manner. In such a scenario the elapsed time is compared with a predetermined threshold in the range of a few seconds, e.g. 10 seconds up to a few minutes, e.g. 5 minutes. According to an example the predetermined threshold is set to 2 minutes. If the time elapsed since the last injection is two minutes or less, the processor 112 stores information indicating that the dosage was delivered as a "split dose".

Another optional purpose for monitoring the elapsed time by the processor 112 is to determine when the elapsed time has passed a predetermined threshold, suggesting that the user might have forgotten to administer another injection and, if so, generate an alert.

LIST OF REFERENCE NUMBERS

1 injection device
2 distal direction
3 proximal direction
4 dose incrementing direction
5 dose decrementing direction
6 cartridge
7 bung
8 drive mechanism
9 dose setting mechanism
10 housing

11 trigger
12 dose dial
13 dosage window
14 cartridge holder
15 injection needle
16 inner needle cap
17 outer needle cap
18 protective cap
19 protrusion
20 piston rod
21 bearing
22 first thread
23 pressure foot
24 second thread
25 barrel
26 seal
28 threaded socket
30 drive sleeve
31 threaded section
32 flange
33 flange
35 last dose limiter
36 shoulder
40 spring
42 recess
50 dose tracker
51 tracking stop feature
60 clutch
62 insert piece
64 stem
80 number sleeve
81 groove
90 ratchet mechanism
91 ratchet feature
100 add-on device
101 housing
102 printed circuit board
110 sensor arrangement
112 processor
114 memory
115 timer
116 output
118 display
120 power source
122 switch
124 interface
126 transceiver
140 insert
141 skirt
150 pressure piece
151 disc section
152 stem
160 accommodation space
190 ratchet mechanism
200 rotation sensor
201 rotatable element
202 wheel
204 spoke
206 spoke
207 outer portion
208 rim
209 inner portion
210 hub
211 middle portion
212 ratchet feature
214 beveled edge
216 flank 220 sensor
222 sensor
224 sensor
226 strain gauge
228 strain gauge
240 counter ratchet feature
241 flexible arm
242 protrusion
244 beveled edge
246 flank
260 diagram
262 drop
280 measurement circuit
281 reference resistor
282 reference resistor
283 node
284 current source
285 node
340 counter ratchet feature
341 flexible arm
342 protrusion
344 beveled edge
346 flank

The invention claimed is:

1. A rotation sensor for an injection device, the rotation sensor comprising:

a rotatable element comprising an outer rim and a hub configured for transmission of a torque between the outer rim and the hub, wherein the rotatable element comprises at least one ratchet feature configured to periodically engage with at least one counter ratchet feature when the rotatable element is subject to a rotation relative to the counter ratchet feature;

at least one sensor attached to, and rotationally fixed relative to, the rotatable element, and configured to measure a rotation of the rotatable element as the at least one sensor rotates with the rotatable element relative to the counter ratchet feature while the at least one ratchet feature periodically engages with the at least one counter ratchet feature; and a processor connected to the at least one sensor and configured to calculate an angle of rotation of the rotatable element based on a sensor output of the at least one sensor.

2. The rotation sensor according to claim 1, wherein the at least one sensor is arranged on the outer rim.

3. The rotation sensor according to claim 1, wherein the rotatable element comprises at least two spokes and wherein the outer rim and the hub are connected via the at least two spokes.

4. The rotation sensor according to claim 3, wherein the at least one sensor is attached to at least one of the at least two spokes.

5. The rotation sensor according to claim 3, wherein at least one of the at least two spokes comprises an outer portion connected to the outer rim, an inner portion connected to the hub and a middle portion connecting the outer portion and the inner portion and wherein one of the inner portion, the middle portion, or the outer portion comprises a cross-section that is smaller than a cross-section of another one of the inner portion, the middle portion or the outer portion.

6. The rotation sensor according to claim 5, wherein a cross-section of the middle portion is smaller than a cross-section of at least one of the outer portion or the inner portion.

7. The rotation sensor according to claim 5, wherein the at least one sensor is arranged on the one of the inner portion, the middle portion, or the outer portion having the cross-section that is smaller than the cross-section of the other one of the inner portion, the middle portion and the outer portion.

8. The rotation sensor according to claim 3, wherein at least one of the at least two spokes is configured to elastically deform when a torque is transmitted between the hub and the rim.

9. The rotation sensor according to claim 1, wherein the at least one sensor comprises at least one of a quantum tunneling composite QTC, a force-sensing resistor, or a strain gauge integrated into the rotatable element or adhesively attached to a portion of the rotatable element.

10. The rotation sensor according to claim 1, wherein at least one of the ratchet feature or the counter ratchet feature comprises a flexible or pivotable arm configured to flex or to pivot relative to the other one of the ratchet feature or the counter ratchet feature to enable a rotation of the ratchet feature past the at least one counter ratchet feature.

11. The rotation sensor according to claim 1, wherein the processor is configured to detect a temporal variation of an amplitude of the sensor output.

12. The rotation sensor according to claim 1, wherein the rotation sensor is attachable to the injection device such that the rotatable element is rotationally lockable to one of a dial member of the injection device or one of a housing and a trigger of the injection device and is rotatable relative to the other one of the dial member or one of the housing and the trigger via a ratchet mechanism.

13. The rotation sensor according to claim 1, wherein the rotatable element is rotatable relative to the counter ratchet feature only along a first sense of rotation and prevented or inhibited to rotate relative to the counter ratchet feature along an opposite second sense of rotation.

14. The rotation sensor according to claim 1, wherein the ratchet mechanism enables a rotation of the rotatable element relative to the counter ratchet feature only along a first sense of rotation.

15. The rotation sensor according to claim 1, wherein the ratchet mechanism prevents or inhibits a rotation of the rotatable element relative to the counter ratchet feature along a second sense of rotation.

16. An injection device for setting and expelling of a dose of a medicament, the injection device comprising:

a housing;

a trigger to initiate and/or to control expelling of the dose;

a dial member rotatable relative to the housing for setting of the dose;

a ratchet mechanism; and a rotation sensor comprising:

a rotatable element mechanically engaged with the ratchet mechanism, the rotatable element comprising an outer rim and a hub configured for transmission of a torque between the outer rim and the hub, at least one sensor attached to, and rotationally fixed relative to, the rotatable element, and configured to measure a rotation of the rotatable element as the at least one sensor rotates with the rotatable element relative to the housing while engaged with the ratchet mechanism, and a processor connected to the at least one sensor and configured to calculate an angle of rotation of the rotatable element based on a sensor output of the at least one sensor, wherein the rotatable element is rotationally locked to one of the dial member and the housing and wherein the rotatable element is rotatable relative to the other one of the dial member and the housing via the ratchet mechanism.

17. The injection device according to claim 16, wherein the at least one sensor is arranged on the outer rim.

18. The injection device according to claim 16, wherein the rotatable element comprises at least two spokes and wherein the outer rim and the hub are connected via the at least two spokes.

19. The injection device according to claim 18, wherein the at least one sensor is attached to at least one of the at least two spokes.

20. The injection device according to claim 18, wherein at least one of the at least two spokes comprises an outer portion connected to the outer rim, an inner portion connected to the hub and a middle portion connecting the outer portion and the inner portion and wherein one of the inner portion, the middle portion, or the outer portion comprises a cross-section that is smaller than a cross-section of another one of the inner portion, the middle portion or the outer portion.

21. The injection device according to claim 20, wherein a cross-section of the middle portion is smaller than a cross-section of at least one of the outer portion or the inner portion.

\* \* \* \* \*